(12) United States Patent
Baldridge et al.

(10) Patent No.: US 10,774,017 B2
(45) Date of Patent: *Sep. 15, 2020

(54) CATALYTIC ACTIVATION OF ISOPENTANE-ENRICHED MIXTURES

(71) Applicant: PHILLIPS 66 COMPANY, Houston, TX (US)

(72) Inventors: Anthony O. Baldridge, Bartlesville, OK (US); Neal D. McDaniel, Ochelata, OK (US); James A. Suttil, Bartlesville, OK (US); Soumen Kundu, Pearland, TX (US); Jianhua Yao, Bartlesville, OK (US); Bruce B. Randolph, Bartlesville, OK (US); Maziar Sardashti, Timnath, CO (US); Steven E. Lusk, Ponca City, OK (US); Robert M. Walston, Jr., Skiatook, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,737

(22) Filed: Mar. 26, 2019

(65) Prior Publication Data

US 2019/0300454 A1    Oct. 3, 2019

Related U.S. Application Data

(60) Provisional application No. 62/648,570, filed on Mar. 27, 2018.

(51) Int. Cl.
*C07C 5/333* (2006.01)
*C10L 1/04* (2006.01)
(Continued)

(52) U.S. Cl.
CPC ............... *C07C 5/333* (2013.01); *C07C 2/42* (2013.01); *C07C 2/54* (2013.01); *C07C 2/56* (2013.01);
(Continued)

(58) Field of Classification Search
CPC .. C07C 5/333; C07C 9/16; C07C 9/18; C07C 9/14; C07C 9/15; C07C 2/74; C07C 2/54;
(Continued)

(56) References Cited

U.S. PATENT DOCUMENTS 7,485,768 B1 * 2/2009 Rice ..................... C10G 35/00
208/133
8,324,441 B2 12/2012 Wegerer et al.
(Continued)

*Primary Examiner* — Ali Z Fadhel
(74) *Attorney, Agent, or Firm* — Phillips 66 Company

(57) ABSTRACT

The present disclosure relates generally to processes and systems for producing liquid transportation fuels by converting a feed stream that comprises both isopentane and n-pentane, and optionally, some C6+ hydrocarbons. Isopentane and smaller hydrocarbons are separated to form a first fraction while n-pentane and larger components of the feed stock form a second fraction. Each fraction is then catalytically-activated in a separate reaction zone with a separate catalyst, where the conditions maintained in each zone maximize the conversion of each fraction to olefins and aromatics, while minimizing the production of C1-C4 light paraffins. In certain embodiments, the first fraction is activated at a lower temperature than the second fraction. The process provides increased yields of upgraded hydrocarbon products that possess the characteristics of a liquid transportation fuel or a blend component thereof.

15 Claims, 6 Drawing Sheets

(51) Int. Cl.
    *C07C 5/32*    (2006.01)
    *C07C 2/76*    (2006.01)
    *C10G 59/06*   (2006.01)
    *C07C 6/10*    (2006.01)
    *C07C 6/12*    (2006.01)
    *C07C 4/06*    (2006.01)
    *C07C 4/10*    (2006.01)
    *C07C 4/02*    (2006.01)
    *C07C 2/74*    (2006.01)
    *C07C 2/54*    (2006.01)
    *C07C 2/56*    (2006.01)
    *C07C 2/58*    (2006.01)
    *C07C 2/42*    (2006.01)
    *C07C 9/16*    (2006.01)
    *C07C 9/18*    (2006.01)
    *C07C 9/14*    (2006.01)
    *C07C 9/15*    (2006.01)

(52) U.S. Cl.
CPC ............... *C07C 2/58* (2013.01); *C07C 2/74* (2013.01); *C07C 2/76* (2013.01); *C07C 4/02* (2013.01); *C07C 4/06* (2013.01); *C07C 4/10* (2013.01); *C07C 5/32* (2013.01); *C07C 5/321* (2013.01); *C07C 6/10* (2013.01); *C07C 6/123* (2013.01); *C07C 6/126* (2013.01); *C07C 9/14* (2013.01); *C07C 9/15* (2013.01); *C07C 9/16* (2013.01); *C07C 9/18* (2013.01); *C10G 59/06* (2013.01); *C10L 1/04* (2013.01); *C07C 2529/40* (2013.01); *C10G 2300/1081* (2013.01); *C10G 2400/20* (2013.01); *C10G 2400/30* (2013.01)

(58) Field of Classification Search
CPC .... C07C 2/56; C07C 2/58; C07C 2/42; C07C 4/06; C07C 4/10; C07C 4/02; C07C 5/32; C07C 6/10; C07C 6/123; C07C 6/126; C07C 5/321; C07C 2/76; C07C 2529/40; C10L 1/04; C10G 59/06; C10G 2400/30; C10G 2300/1081; C10G 2400/20; C10G 9/00; C10G 57/005; C10G 29/205
See application file for complete search history.

(56) References Cited

U.S. PATENT DOCUMENTS

2010/0036182 A1*   2/2010   Forestiere .............. C07C 11/06
    585/251
2010/0041930 A1*   2/2010   Gartside ................ C07C 11/06
    585/314

\* cited by examiner

CATALYTIC ACTIVATION OF ISOPENTANE-ENRICHED MIXTURES

CROSS-REFERENCE TO RELATED APPLICATIONS

This application is a non-provisional application which claims the benefit of and priority to U.S. Provisional Application Ser. No. 62/648,570 filed Mar. 27, 2018, titled "Catalytic Activation of Isopentane-Enriched Mixtures," which is hereby incorporated by reference in its entirety.

STATEMENT REGARDING FEDERALLY SPONSORED RESEARCH OR DEVELOPMENT

None.

FIELD OF THE INVENTION

The present disclosure relates to processes and systems for separating isopentane from a feed stream comprising both isopentane and n-pentane, separately activating each isomer to maximize the yield of olefins and aromatics, then optionally further converting to chemicals or liquid hydrocarbon transportation fuels in a subsequent step by alkylation or oligomerization.

BACKGROUND

A large surplus of pentanes are available in the petroleum refining industry, arising predominantly from the increased production of light hydrocarbons from U.S. shale formations, and also from limits on the quantity of volatile components that can be blended into finished transportation fuels, which must adhere to regulations on minimum vapor pressure. Unfortunately, conventional processes for upgrading light alkanes to value-added products are not well-suited for hydrocarbon feed streams that primarily comprise pentanes (i.e., isopentane and n-pentane). Therefore, it would be beneficial to find improved processes and systems for efficiently converting pentanes to more valuable products, including transportation fuels and chemicals, while minimizing the production of C1-C4 light paraffins.

The inventive processes disclosed herein provide an improved upgrading route for pentane-rich mixtures, such as fuel blend stocks and other pentane-rich streams that do not meet government fuel specifications. The inventive processes and systems provide enhanced yields of upgraded products that may be suitable for use as transportation fuels or other value-added chemical products.

BRIEF SUMMARY OF THE DISCLOSURE

The present inventive disclosure relates to methods and systems for converting a mixture predominantly comprising isopentane (i-C5) and n-pentane (n-C5) isomers into products that can be used as a liquid transportation fuel, or a blend component thereof. In certain embodiments, a feed stream comprising pentanes is separated into a first fraction that is enriched in i-C5 (i.e., a first fraction) and a second fraction that is enriched in n-C5. The second fraction may also contain C6+ components including mono-cyclic aromatics. The enriched first fraction is catalytically-cracked to an upgraded intermediate product comprising light olefins and aromatics. The second fraction can be blended directly into liquid transportation fuels or can be catalytically activated to yield light olefins and aromatics. The ratio of olefins to aromatics in the activation product can vary depending upon the conditions utilized. A variety of feed streams that are rich in pentanes can be advantageously upgraded using the inventive processes and systems described herein, including pentanes derived from fractionation of natural gas liquids, as well as natural gasoline pools that cannot be blended into liquid transportation fuels due to governmental restrictions on the maximum vapor pressure of the final fuel that is sold.

Certain embodiments of the process relate to a method for converting a feed stream comprising pentanes to produce a liquid transportation fuel, comprising: a.) providing a hydrocarbon feed stream comprising at least 50 wt. % pentanes, including both n-pentane and isopentane, wherein the hydrocarbon feed stream further comprises less than 10 wt. % of hydrocarbons containing four or fewer carbons; b) at least partially separating various constituents in the hydrocarbon feed stream according to each constituent's characteristic vapor pressure, to produce: i.) a first fraction comprising at least 80% of the isopentane present in the feed stream and at least 90% of hydrocarbons present in the hydrocarbon feed stream that are characterized by a vapor pressure equal to or greater than the vapor pressure of isopentane; ii.) a second fraction that comprises at least 80% of the n-pentane present in the hydrocarbon feed stream and at least 90% of any hydrocarbons containing six or more carbons that were present in the hydrocarbon feed stream; c.) contacting the first fraction with a first activation catalyst at conditions comprising a first temperature and first pressure that facilitate conversion of at least a portion of the first fraction by the first activation catalyst to a first effluent comprising olefins containing from two to five carbon atoms, monocyclic aromatics and unconverted alkanes containing from two to five carbon atoms; d.) contacting at least a portion of the second fraction with a second activation catalyst at a second temperature and second pressure that facilitate conversion of at least a portion of the second fraction by the second catalyst to produce a first effluent comprising olefins containing from two to five carbon atoms, monocyclic aromatics and unconverted alkanes containing from two to five carbon atoms, wherein the first temperature is lower than the second temperature; e.) combining at least a portion of the of the first effluent and the second effluent to produce a mixed activation effluent that is at least partially condensed to produce a mixed liquid hydrocarbons fraction and a light hydrocarbons fraction, wherein the mixed liquid hydrocarbons comprises at least 80 wt. % of one or more of pentene, single-ring aromatics and unreacted alkanes containing at least five carbon atoms, wherein the light hydrocarbons comprises at least 80 wt. % hydrocarbons that contain four or fewer carbon atoms and hydrogen.

Certain embodiment further comprise separating the mixed liquid hydrocarbons into an aromatics fraction and an unreacted C5/C6 hydrocarbons fraction, where the aromatics fraction comprises monocyclic aromatics suitable for use as a blend component of gasoline and the unreacted C5/C6 hydrocarbons fraction comprises alkanes and olefins containing from five to six carbons that may be mixed with the hydrocarbon feed stream. In certain embodiments, a portion of the second fraction is not contacted with the second catalyst, but instead, is blended with the aromatics fraction.

Optionally, the hydrocarbon feed stream comprises less than 5 wt. % of hydrocarbons containing four or fewer carbon atoms. Optionally, the hydrocarbon feed stream comprises at least 60 wt. % pentanes. In certain embodiments, the first temperature is at least 25° C. lower than second temperature, optionally, at least 50° C. lower than second temperature. In certain embodiments, the weight hourly space velocity of the first fraction as it contacts the first catalyst is higher than the weight hourly space velocity of the second fraction as it contacts the second catalyst. The first catalyst optionally differs from the second catalyst in at least one of chemical composition and structural composition.

Certain embodiments additionally comprise adding a diluent to at least one of: the first fraction prior to the contacting of c) and the second fraction prior to the contacting of d), wherein the diluent is characterized as less likely to react with the first catalyst than molecules present in the first fraction at the conditions of temperature and pressure that are maintained in the first reactor, and where the diluent is characterized as less likely to react with the second catalyst than molecules present in the second fraction at the conditions of temperature and pressure that are maintained in the second reactor. Optionally, the diluent does not react catalytically with the first activation catalyst at the conditions of temperature and pressure that are maintained in the first reactor, and also does not react catalytically with the second activation catalyst at the conditions of temperature and pressure that are maintained in the second reactor.

In certain embodiments, adding the diluent alters the specificity of at least one of the first activation catalyst and the second activation catalyst to increase the production of olefins, decrease the production of aromatics, or combinations thereof, thereby increasing the ratio of olefins to aromatics in the mixed effluent. In certain embodiments, the diluent is added in an amount that is effective to produce a mixed effluent comprising an olefins to aromatics ratio in the range of 0.5 to 2.0, optionally in the range from 0.5 to 1.5, optionally in the range from 1.0 to 1.5, optionally in the range of 0.5 to 1.0. In certain embodiments, the diluent is selected from methane, ethane, propane, butanes, benzene, toluene, xylenes, alkyl- or dialkyl-benzenes, naphthenes, C2-C5 olefins, and combinations thereof.

BRIEF DESCRIPTION OF THE DRAWINGS

A more complete understanding of the present invention and benefits thereof may be acquired by referring to the follow description taken in conjunction with the accompanying drawings in which.

Figure 1:
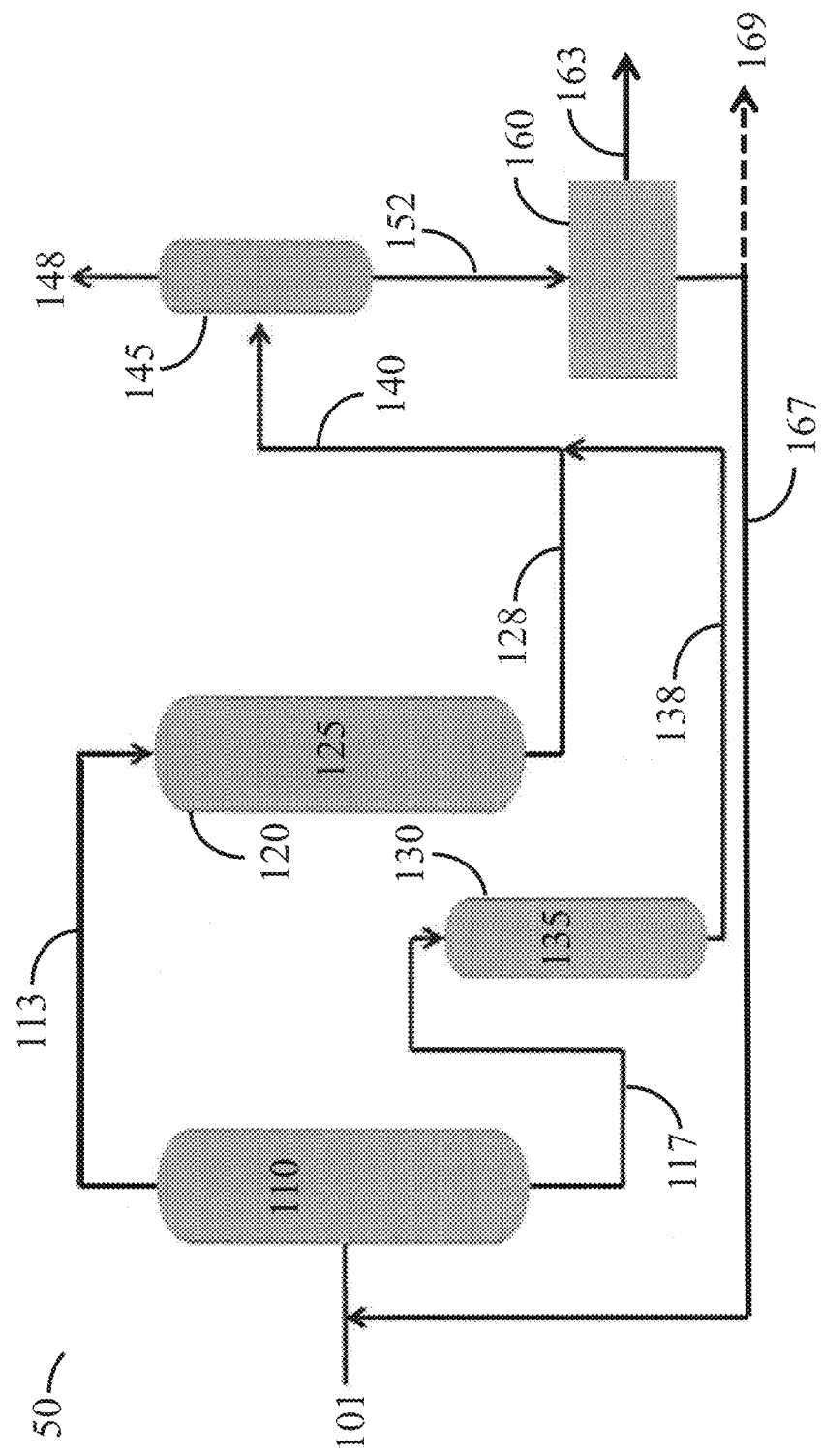
FIG. 1 is a diagram depicting a first embodiment of the inventive processes and systems.

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

The present disclosure provides processes to convert a mixture of light hydrocarbons to liquid transportation fuels. The process and systems described herein relate primarily to the conversion of any hydrocarbon mixture that predominantly comprises pentanes to generate upgraded products that may be sold as a value-added chemical or utilized as a blend component of a liquid transportation fuel.

Generally speaking, the inventive processes and systems described herein utilize a feed stream comprising both isopentane and n-pentane, and perform at least a partial separation of these pentane isomers to generate a first fraction that is enriched in isopentane and smaller hydrocarbons, and a second fraction that largely retains n-pentane and any C6 or larger (C6+) hydrocarbons that were present in the original feed stream. The two streams are catalytically activated in separate activation reactors. For each fraction, the temperature and/or pressure of the fraction (measured at the inlet of its respective activation reactor) is maintained at a value that maximizes the catalytic conversion of that fraction to olefins and aromatics, while minimizing the production of C1-C4 light paraffins. In certain embodiments, the temperature and/or pressure that is maintained in each of the two reactors may be different, based upon the relative reactivity of each fraction to catalytic activation. The resulting first effluent and second effluent are combined, then optionally further upgraded by in a third reactor by oligomerization and/or alkylation to produce value-added chemicals and/or products suitable for use as a liquid transportation fuel blend component.

The present inventive processes and systems take advantage of the differing reactivity of pentane isomers to catalytic activation. Isopentane (i-C5) exhibits catalyst-dependent reactivity that is typically different from n-pentane (n-C5), and the optimal reactor conditions for the two isomers are therefore distinct. Experimentally, isopentane (i-C5) is more reactive than n-pentane (n-C5), and thus, can be activated at lower temperatures while maintaining high yields of desired products (such as olefins and aromatics) and decreasing the yield of C1-C4 paraffins. The inventive system allows activation conditions to be individually tailored for each pentane isomer in a way that cannot be achieved via processes that upgrade a mixed pentane stream. Additional advantages will become evident from the detailed disclosure provided below.

As mentioned, the feed stream generally comprises a stream of light hydrocarbons that comprises a mixture of pentane isomers (C5), although certain embodiments may additionally comprise C1-C4 hydrocarbons, C6-C7 hydrocarbons, or both. In certain embodiments, the feed stream comprises at least 10 wt. % of a mixture of pentane isomers; optionally, at least 20 wt. %, at least 30 wt. %, at least 40 wt. %, at least 50 wt. %, at least 60 wt. %, or at least 70 wt. %. of a mixture of pentane isomers. In certain embodiments, the feed stream may be obtained by processing a stream of natural gas liquids to remove lighter components (i.e., C1-C4) by way of conventional natural gas processing technologies that are well-characterized, such as de-methanizer, de-ethanizer, de-propanizer and de-butanizer fractionation columns. A typical result of such processes is commonly characterized as natural gasoline, comprising about 72 wt. % pentanes, with the remainder mostly comprising C6.

A first embodiment of the inventive processes and systems is illustrated by the process flow-diagram of FIG. 1. A pentane-rich feed stream 101 comprising both n-pentane and isopentane is converted in a system 50. The feed stream 101 is received by a first separation unit 110 that operates to separate the feed stream 101 into a first fraction 113 that comprises an increased wt. % of isopentane (i-C5) relative to the feed stream 101, and a second fraction 117 that comprises an increased wt. % of n-pentane relative to the feed stream 101. The second fraction further comprises a large majority of any C6 and larger (C6+) hydrocarbons that were originally present in the feed stream 101. The first separation unit 110 may operate using conventional separation technology to separate the i-C5 isomer from the remaining compounds present within the C5-rich hydrocarbon feed stream. Alternatively, any other conventional separation technology may be used to assist in separating i-C5 from n-C5 to produce the first fraction and the second fraction.

Following separation, the first fraction 113 is conveyed to a first activation reactor 120 containing a first activation catalyst 125, while the second fraction 117 is introduced into a second reactor 130 containing a second activation catalyst 135. Each of the first and second rectors, respectively, is operable to maintain a temperature and pressure that is suitable to facilitate conversion of the first fraction 113 to a first effluent 128, and the second fraction 117 to a second effluent 138. Speaking generally, the first and second effluent each comprise products that may be utilized as a commodity chemical, an intermediate amenable to further catalytic upgrading, or a transportation fuel (or a component thereof). Each activation catalyst may comprise a single catalyst, or a mixture of different catalysts that contact the alkanes present in a given feed stream and facilitates at least one of dehydrogenation, cracking, and aromatization of the alkanes, thereby producing upgraded products including olefins and aromatics.

Speaking generally, each activation catalyst may comprise any catalyst capable of cracking and/or aromatizing hydrocarbons. Favored catalysts include supported or unsupported solid acids, metals, metal chalcogenides, or metal pnictogenides, including (but not limited to) structured and amorphous silica-aluminas, structured and amorphous solid phosphoric acids, clays, other metal oxides, metal sulfates, or metal phosphates, and graphite-supported materials. In certain embodiments, ZSM-5 zeolite catalysts are utilized that are characterized by Si/Al ratios ranging from 12-80, optionally ranging from 35 to 50. Optionally, one or more elements may be impregnated on the zeolite catalyst, including one or more of Ga, Pt, Ni, Mn, Mg, Fe, Cr, P, Cu, La, Sr and F.

Optionally, the activation catalyst utilized in the first catalytic activation zone is different from the activation catalyst utilized in the second catalytic activation zone. Generally speaking, dehydrogenation catalysts are not a prerequisite of paraffin activation in the inventive process. A sufficient concentration of intermediate olefins can be generated through a combination of thermal dehydrogenation and catalytic cracking such that typical dehydrogenation metals (such as platinum, zinc, molybdenum, or gallium) can be avoided without significantly decreasing product yield. Known dehydrogenation catalysts are prone to fouling by sulfur and nitrogen contaminants that are often present in hydrocarbon feed streams derived from petroleum, so the ability to operate in the absence of sensitive catalytic materials is highly advantageous.

The inventive process generally takes advantage of the large difference in catalytic reactivity between n-C5 and i-C5. For example, over a solid acid catalyst at temperature in excess of 550° C., the measured activation rates differ by up to 4 fold in favor of i-C5, when each isomer is contacted with the same catalyst under identical conditions (even in the same reactor simultaneously). Thus, an at least partial separation of the mixed pentanes feed stream to form a first fraction that largely comprises i-C5 and a second fraction that retains a large majority of the n-C5 in the feed stream, followed by separately activating each fraction in a distinct catalytic activation zone, allows each pentane isomer to be upgraded with an optimal catalyst and conditions of temperature and pressure that maximize the yield of value-added, upgraded products (such as olefins and/or aromatics). Separation of the isomers also helps to minimize selectivity to C1-C4 light paraffins.

Table 1 (below) illustrates the difference in the activation reactivity of i-C5 versus n-C5 over a microporous silica-alumina catalyst. Feed streams comprising either 100 wt. % i-C5 or 100 wt. % n-C5 were each catalytically activated in separate experiments utilizing temperatures of either 600° C. or 550° C. The conversion and product distribution for i-C5 are shown in Table 1, columns 2 and 3, while similar results for the activation of n-C5 are shown in Table 1, columns 4 and 5. The data shows that when comparing the activation of pentane isomers, conversion of i-C5 to olefins and aromatics is possible at a temperature about 50° C. less than is required for equivalent conversion of n-C5. To be clear, we observed that activation of the i-C5 feed stream at 550° C. converted about the same weight percentage of the feed stream as did activation of n-C5 at 600° C. using the same WHSV. Further, utilizing a decreased temperature of 550° C. for activation of the i-C5 feed stream advantageously decreased the production of C1-C4 light paraffins from 21.0% to 19.4% by increasing the product distribution toward olefins rather than aromatic products. Thus, the ability to separate the i-C5 isomer from n-C5 isomer (and any C6+ hydrocarbons) and activate the i-C5 enriched mixture at relatively reduced temperature, results in approximately equivalent total conversion of the overall feed stream, while decreasing the formation of undesired C1-C4 light paraffins.

Referring again to the embodiment illustrated in FIG. 1, the first fraction 113 enters an inlet of the first activation reactor 125. The temperature within the first activation reactor 125 (typically measured at the inlet of the first activation reactor) is maintained in the range from 500° C. to 650° C.; optionally, within the range from 525° C. to 625° C.; optionally, within the range from 525° C. to 600° C.; optionally, within the range from 550° C. to 600° C.; optionally, within the range from 550° C. to 575° C.

The second fraction 117 enters an inlet of the second reactor 135. The temperature within the second reactor 135 (typically measured at the inlet of the second reactor) is maintained in the range from 500° C. to 650° C. Optionally, the temperature is maintained within the range from 525° C. to 650° C. Optionally, the temperature is maintained within the range from 550° C. to 625° C. Optionally, the temperature is maintained within the range between 575° C. and 600° C. Lower pressure favors the conversion of light alkanes to light olefins. Thus, the first activation reactor 125 and second reactor 135 are generally maintained at a pressure ranging from 15 psia to 165 psia. In certain embodiments, the pressure is maintained in the range from 15 psia to 50 psia.

In certain embodiments, the temperature maintained within the first activation reactor (first temperature, typically measured at the inlet of the first activation reactor) is lower than the temperature maintained at the inlet of the second activation reactor (second temperature, typically measured at the inlet of the second activation reactor). Optionally, the first temperature may be at least 10° F. lower, at least 20° F. lower, at least 25° F. lower, at least 30° F. lower, at least 35° F. lower, at least 40° F. lower, at least 45° F. lower or at least 50° F. lower than the second temperature. Utilizing a lower temperature for the conversion of the first fraction 113 allows approximately equivalent conversion to upgraded products that may be blended into liquid transportation fuel or sold as chemical feed streams, while minimizing the production of undesirable light hydrocarbons containing four or fewer carbons.

Referring again to the embodiment depicted in FIG. 1, the first effluent 128 is combined with the second effluent 138 to form a mixed activation effluent 140 that predominantly comprises C2-C5 olefins, single-ring aromatics, hydrogen and unreacted alkanes that were present in hydrocarbon feed stream 101. Speaking generally, Table 1 details the molecular profile for examples of either a first effluent (comprising i-C5) and a second effluent (comprising n-C5) each being activated at temperatures of 550° C. and 600° C., respectively.

TABLE 1

Product distributions for i-C5 or n-C5 isomer feed streams following conversion by a ⅛" extrudate consisting of 50 wt. % alumina binder and 50 wt. % ZSM-5 zeolite. Activation was performed by contacting the ZSM-5 catalyst with a feed stream comprising either 100 wt. % of i-C5 or 100 wt % of n-C5. Results were time-averaged over 16 hours and all reactions were performed at 1 atm with a WHSV = 4.0 $hr^{-1}$.

| | Feed Isomer: | | | |
|---|---|---|---|---|
| | i-C5 | i-C5 | n-C5 | n-C5 |
| | | Inlet Temperature: | | |
| | 600° C. | 550° C. | 600° C. | 550° C. |
| | | Conversion (wt. %): | | |
| | 94.5 | 82.4 | 78.5 | 48.3 |
| | | Product Distribution (wt. %) | | |
| Hydrogen | 2.4% | 1.6% | 1.1% | 0.4% |
| Methane | 9.8% | 7.8% | 5.3% | 2.3% |
| Ethane | 3.0% | 2.6% | 11.5% | 6.6% |
| Ethylene | 17.4% | 15.6% | 14.3% | 7.7% |
| Propane | 5.3% | 4.8% | 10.6% | 9.9% |
| Propylene | 21.2% | 22.1% | 16.4% | 10.3% |
| Butane | 2.9% | 4.2% | 0.8% | 1.2% |
| Butene | 8.5% | 9.9% | 5.8% | 5.5% |
| Isopentane | 5.5% | 17.6% | 0.1% | 0% |
| n-Pentane | 0% | 0% | 21.5% | 51.7% |
| Pentene | 1.2% | 1.8% | 0.8% | 1.2% |
| C6+ alkanes | 0.0% | 0.3% | 0.0% | 0.0% |
| Benzene | 4.8% | 3.3% | 4.9% | 1.0% |
| Toluene | 11.1% | 6.0% | 5.3% | 1.6% |
| Xylene | 6.4% | 2.2% | 1.3% | 0.6% |
| EB | 0.3% | 0.1% | 0.1% | 0.0% |
| Coke | 0.2% | 0.1% | 0.2% | 0.1% |

Referring again to the embodiment depicted in FIG. 1, the mixed activation effluent 140 is conveyed into a second separator 145 that separates hydrogen and light hydrocarbons 148 containing four or fewer carbons from a mixed liquid hydrocarbons 152 that predominantly comprises C5 olefins, single-ring aromatics as well as unreacted pentanes and larger C6+ components present in the hydrocarbon feed stock 101. In certain embodiments, the second separator 145 is a two-phase splitter and separation of the mixed activation effluent 140 is achieved by partial condensation. The light hydrocarbons 148 can be either combusted for heat generation or diverted to other upgrading processes that are outside the scope of this disclosure. The mixed liquid hydrocarbons 152 is next conveyed to a conventional naphtha stabilizer 160 that separates the mixed liquid hydrocarbons 152 into an aromatics fraction 163 (predominantly comprising aromatics) and an unreacted C5/C6 components fraction 167 that predominantly comprises unreacted pentanes and larger C6+ components. The unreacted C5/C6 components fraction 167 may optionally be recycled and reintroduced upstream from the first separator 110 or utilized directly as a gasoline blend component 169.

Certain embodiments of the inventive processes and systems convey a mixed effluent (derived by mixing at least a portion of the effluent from the first and second activation reactors) to an oligomerization reactor containing at least one oligomerization catalyst. The mixed effluent contacts the oligomerization catalyst and is converted to larger hydrocarbon products that can be utilized as a component of a liquid transportation fuel, such as, but not limited to: gasoline, diesel and jet fuel.

Figure 2:
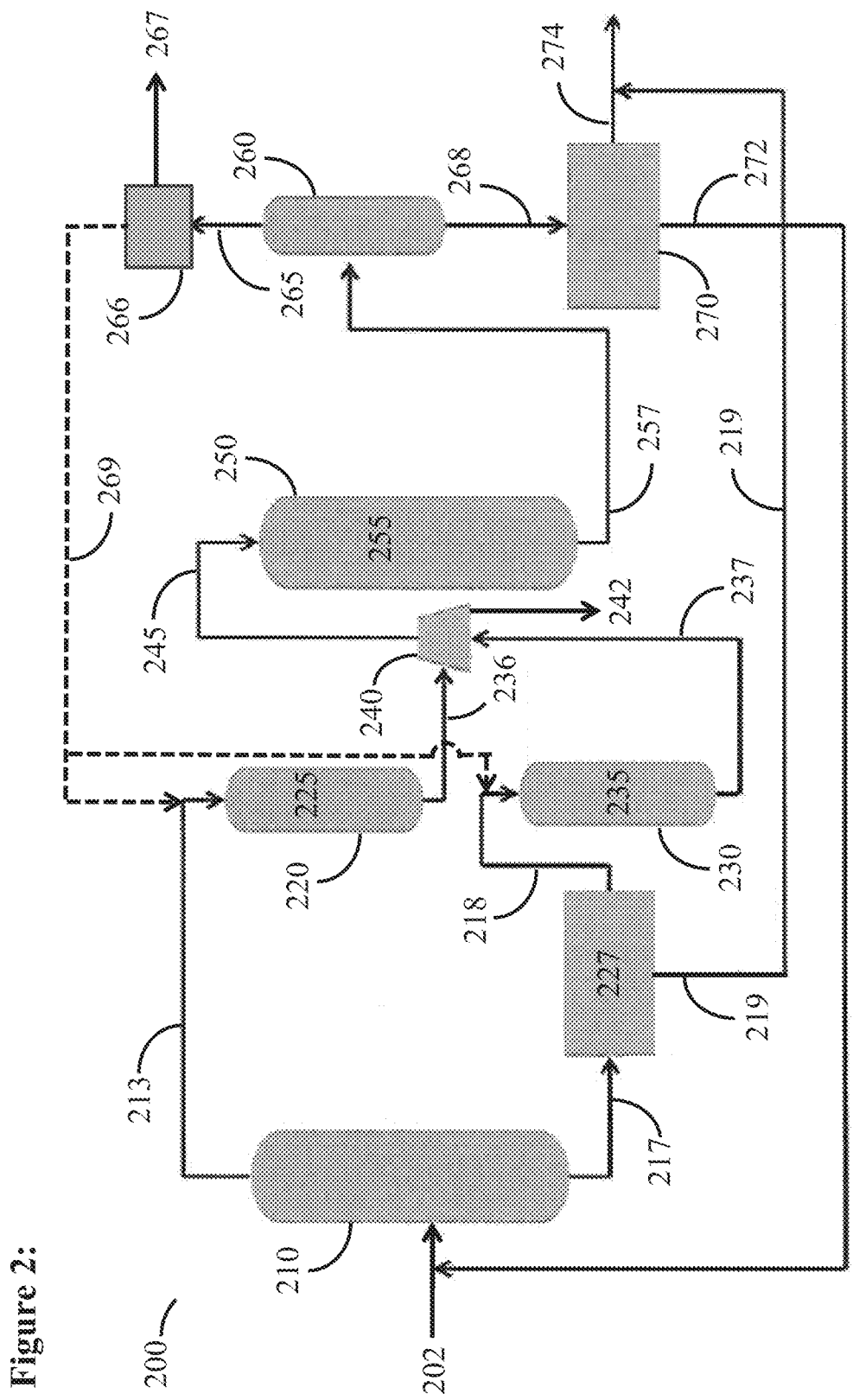
FIG. 2 is a diagram depicting a second embodiment of the inventive processes and systems.

A second embodiment of the inventive processes and systems that includes an oligomerization reactor and additional inventive features is illustrated by the process flow-diagram of FIG. 2. A feed stream 202 comprising both n-C5 and i-C5 is converted in a system 200. The feed stream 202 is received by a first separation unit 210 that is operable to separate the feed stream 202 into a first fraction 213 that comprises an increased wt. % of isopentane (i-C5) relative to the feed stream 202, and a second fraction (i.e., n-C5/C6+ fraction) 217 that comprises an increased wt. % of n-pentane (n-C5) relative to the feed stream 202. The second fraction 217 additionally comprises a large majority of any hydrocarbons containing six or more carbon atoms that were originally present in the feed stream 202.

The first separation unit 210 uses conventional separation technology understood by those having experience in petroleum refining. In one embodiment, separation unit 210 may be a deisopentanizer that is operable to separate the i-C5 isomer from the remaining compounds present within the feed stream 202. Alternatively, any other conventional separation technology may be used to assist in separating i-C5 from n-C5 to produce the first fraction and the second fraction. Such technology is conventional, and thus, outside the scope of the present disclosure.

Upon leaving the first separation unit 210, the first fraction 213 is conveyed into a first activation reactor 220 containing a first catalyst 225, while the second fraction 217 is conveyed into a storage vessel 227 comprising at least two outlets: a first outlet that allows a first portion of the second fraction 218 to be directed to a second activation reactor 230 containing a second activation catalyst, and a second outlet that controls the flow rate of a second portion of the second fraction 219 that is diverted and blended with the final liquid hydrocarbon product of the inventive process and system (discussed in greater detail below). The second activation reactor 230 contains a second catalyst 235. Certain embodiments do not require a storage vessel. In such embodiments, any excess second fraction that is not directed to the second activation reactor is diverted and conveyed for blending with the final liquid hydrocarbon product of the inventive process and system (discussed in greater detail below).

Speaking generally, the first activation reactor and second activation reactor are operable to maintain a temperature and a pressure that are suitable to facilitate either catalytic conversion of the first fraction by the first catalyst, or catalytic conversion of the second fraction by the second catalyst to produce products that may be utilized as a commodity chemical, an intermediate amenable to further catalytic upgrading, or liquid transportation fuel (or a blend component thereof).

Referring again to the embodiment outlined in FIG. 2, the first fraction 213 enters an inlet of the first activation reactor 225. The temperature within the first activation reactor (termed the first temperature, typically measured within the inlet of the first activation reactor) is maintained in the range from 500° C. to 650° C.; optionally, the temperature is maintained in the range from 525° C. to 625° C.; optionally, the temperature is maintained in the range from 525° C. to 600° C.; optionally, the temperature is maintained in the range from 550° C. to 600° C.; optionally, the temperature is maintained in the range from 550° C. to 575° C.

The second fraction 217 enters an inlet of the second activation reactor 235. The temperature within the second activation reactor 235 (termed the second temperature, typically measured within the inlet of the second activation reactor) is maintained in the range from 500° C. to 650° C. Optionally, the temperature is maintained in the range from 525° C. to 650° C. Optionally, the temperature is maintained in the range from 550° C. to 625° C. Optionally, the temperature is maintained in the range between 575° C. and 600° C. Lower pressure favors the conversion of light alkanes to light olefins. Thus, the first activation reactor 225 and second activation reactor 235 are generally maintained at a pressure ranging from 15 psia to 165 psia. In certain embodiments, the pressure is maintained in the range from 15 psia to 50 psia.

In certain embodiments, the first temperature is lower than the second temperature. Optionally, the first temperature may be at least 10° F. lower, at least 20° F. lower, at least 25° F. lower, at least 30° F. lower, at least 35° F. lower, at least 40° F. lower, at least 45° F. lower or at least 50° F. lower than the second temperature.

Each of the first and second activation catalysts may comprise a single catalyst, or a mixture of chemically- and/or structurally-different catalysts that contact the alkanes present in a given feed stream and facilitate at least one of dehydrogenation, cracking, and aromatization of the alkanes, thereby producing an effluent that predominantly comprises light paraffins that contain from one to four carbons (C1-C4 paraffins), C2-C5 olefins and single ring aromatic compounds (see Table 1).

A first effluent 236 leaves the first activation reactor 220, while a second effluent 237 leaves the second activation reactor 230. Each effluent is conveyed to condenser 240, which may comprise one or more functions including a condenser, splitter, compressor and pump. Condenser 240 is operable to receive and combine the first effluent 236 and the second effluent 237 and condense liquids from the mixture to produce a mixed liquid hydrocarbons and a gas-phase mixed effluent 245 (that is gaseous). The mixed liquid hydrocarbons 242 are removed while the mixed effluent 245 is then compressed either within the condenser 240 or by a separate compressor located immediately downstream (not depicted), and then conveyed to an oligomerization reactor 250 that contains an oligomerization catalyst 255.

Speaking generally, the oligomerization catalyst may comprise any solid catalyst (or mixture of catalysts) characterized as possessing either Brønsted or Lewis acidic properties. In certain embodiments, the oligomerization catalyst is a zeolite or mixture of zeolites, or a reactive transition metal oxide. In certain embodiments, the oligomerization catalyst is ZSM-5, although many zeolites are well-characterized as possessing oligomerization properties and may be suitable for use (either alone or in combination) with the inventive processes and systems described herein. Other well-characterized oligomerization catalysts include, but are not limited to: nickel oxides, aluminum alkyls, aluminum halides, perfluoroaryl boranes, oligomeric methyl aluminoxanes (including supported), perfluoroaryl boranes, fluoroarylanes, trityl borate, ammonium borate (and aluminate salts thereof), supported PhNMe2H+B(C6F5)4- and borate anions and superacidic solid Brønsted acids, among others.

Speaking generally, the oligomerization reactor is maintained at a temperature and pressure suitable to facilitate oligomerization of olefins present in the mixed effluent, thereby producing larger hydrocarbons comprising at least six carbons that are preferably characterized by a boiling point that is in the boiling point range of a liquid transportation fuel (e.g., gasoline or diesel). The oligomerization reactor is generally maintained at a total pressure in a range from 14 psia to 800 psia, optionally in the range from 50 psia to 300 psia. The oligomerization reactor is typically maintained at a temperature (measured within the oligomerization reactor inlet) in the range from 200° C. to 420° C., optionally in the range from 200° C. to 350° C. Typically, flow thorough the oligomerization reactor is maintained at a weight hourly space velocity (WHSV) in the range from 0.5 $hr^{-1}$ to 10 $hr^{-1}$. Optionally, the WHSV is in the range from 0.5 $hr^{-1}$ to 2.0 $hr^{-1}$. While higher overall throughput is desirable, ideally the chosen WHSV allows for conversion of at least 85% of hydrocarbons present in the mixed effluent at the selected operating temperature and pressure.

The catalytic conversion occurring in the oligomerization reactor produces an oligomerization effluent that typically comprises an increased quantity of hydrocarbon molecules that are characterized by a boiling-point in the range of gasoline. Preferably, the combination of and subsequent oligomerization converts at least 30 wt % of the original feed stream to hydrocarbon molecules that are characterized by a boiling point that is in the range of gasoline.

Referring again to the embodiment depicted in FIG. 2, the oligomerization effluent 257 is conveyed to a second separator 260 that separates the oligomerization effluent 257 into two fractions: a light hydrocarbons fraction 265 comprising C1-C4 hydrocarbons and hydrogen, and a condensable liquid hydrocarbons fraction 268 comprising hydrocarbons containing at least five carbon atoms (C5+) that may be utilized directly as a blend component of a liquid transportation fuel or an intermediate product that may be additionally processed prior to blending into a liquid transportation fuel.

In certain embodiments, the condensed liquid hydrocarbons 268 may be conveyed to a third separator 270 that in certain embodiments is a naphtha stabilizer. In certain embodiments the third separator 270 is operable to remove a recycle fraction 272 (comprising predominantly alkanes and olefins containing four to six carbon atoms) from the condensed liquid hydrocarbons 268 in order to decrease Reid vapor pressure and increase octane rating. The resulting liquid hydrocarbon product 274 predominantly comprises hydrocarbon molecules that are characterized by a boiling-point in the range of a liquid transportation fuel, such as, but not limited to, gasoline, diesel and jet fuel. The recycle fraction 272 is combined with feed stream 202 at a point that is upstream from the first separation unit 210. Optionally, a portion of the second fraction that is stored in storage vessel 227 may be directed via excess second fraction conduit 219 to be combined with liquid hydrocarbon product 274.

Speaking more generally, in certain embodiments the liquid hydrocarbon product may be hydrotreated in a hydrotreating reactor containing a hydrotreating catalyst in order to reduce olefins and aromatic content in the liquid hydrocarbon product, as well as to remove nitrogen-containing and sulfur-containing compounds. The hydrotreating reactor contains at least one hydrotreating catalyst (such as, for example, NiMo, CoMo, etc.) or a precious metal catalyst (such as $Pt/Al_2O_3$, $Pd/Al_2O_3$, or Pd/C, etc) and is maintained at a pressure and temperature suitable for facilitating hydrotreating catalytic reactions. Such processes are conventional in nature and therefore will not be described in greater detail here.

Again, referring to the embodiment depicted in FIG. 2, light hydrocarbons fraction 265 predominantly comprises hydrogen as well as C1-C4 hydrocarbons that were not converted in the oligomerization reactor 255. Light hydrocarbons fraction 265 leaves the second separator 260 and is optionally conveyed to a fourth separator 266 that utilizes a conventional separation technology (such as, but not limited to, pressure swing adsorption technology, membrane separation technology, etc.) to separate hydrogen from light hydrocarbons to produce a hydrogen stream 267 and a C1-C4 light paraffins stream 269 that may be combusted to provide at least a portion of the heat required for the process, or recycled to serve as a diluent that is mixed with at least one of: the first fraction 213 and the second fraction 218.

Certain embodiments of the inventive processes and systems combine the effluent from each of the first and second activation reactors, then convey the resulting mixture to an aromatic alkylation reactor containing at least one alkylation catalyst. The mixed effluent contacts the alkylation catalyst and is converted to larger hydrocarbon products that can be utilized as either gasoline or diesel transportation fuel, or a component thereof.

Figure 3:
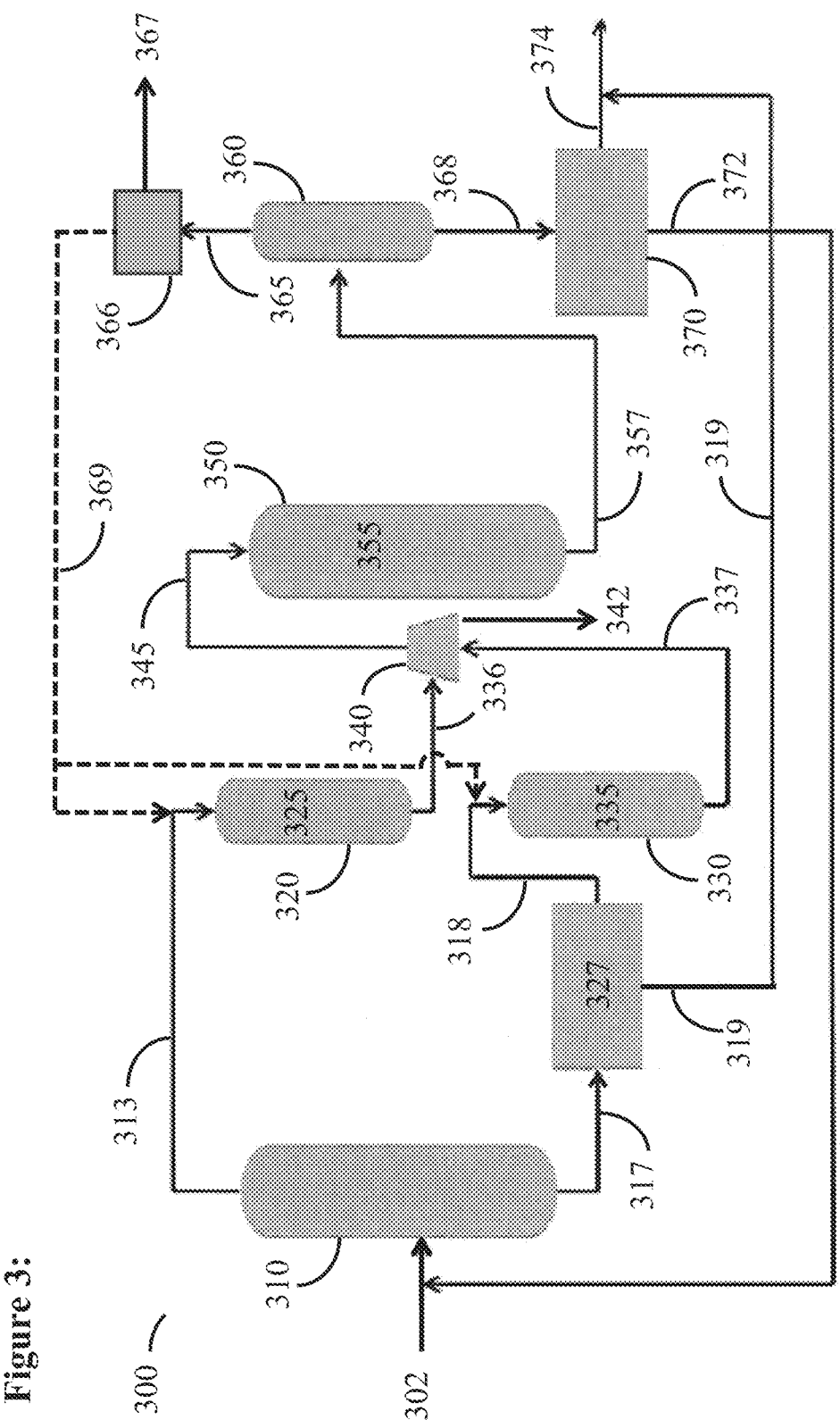
FIG. 3 is a diagram depicting a third embodiment of the inventive processes and systems.

A third embodiment of the inventive processes and systems that includes an alkylation reactor and additional inventive features is illustrated by the process flow-diagram of FIG. 3. A feed stream 302 comprising both n-C5 and i-C5 is converted in a system 300. The feed stream 302 is received by a first separation unit 310 that is operable to separate the feed stream 302 into a first fraction 313 that comprises an increased wt % of isopentane (i-C5) relative to the feed stream 302, and an second fraction (i.e., n-C5/C6+ fraction) 317 that comprises an increased wt. % of n-pentane (n-C5) relative to the feed stream 302. The second fraction 317 additionally comprises a large majority of any hydrocarbons containing six or more carbon atoms that were originally present in the feed stream 302.

The first separation unit 310 uses conventional separation technology understood by those having experience in petroleum refining. In one embodiment, separation unit 310 may be a deisopentanizer that is operable to separate the i-C5 isomer from the remaining compounds present within the feed stream 302. Alternatively, any other conventional separation technology may be used to assist in separating i-C5 from n-C5 to produce the first fraction and the second fraction.

Upon leaving the first separation unit 310, the first fraction 313 is conveyed into a first reactor 320 containing a first activation catalyst 325, while the second fraction 317 is conveyed into a storage vessel 327 comprising at least two outlets: a first outlet that allows a first portion of the second fraction 318 to be conveyed to a second activation reactor 330 containing a second activation catalyst 335, and a second outlet that controls the flow rate of a second portion of the second fraction 319 that is diverted and blended with the final liquid hydrocarbon product 374 of the inventive process and system (discussed in greater detail below). Certain embodiments do not require a storage vessel. In such embodiments, any excess second fraction that is not directed to the second activation reactor is diverted and conveyed for blending with the final liquid hydrocarbon product of the inventive process and system (discussed in greater detail below).

Speaking generally, the first activation reactor and second activation reactor are operable to maintain a temperature and a pressure that are suitable to facilitate either catalytic conversion of the first fraction by the first catalyst, or catalytic conversion of the second fraction by the second catalyst to produce products that may be utilized as a commodity chemical, an intermediate amenable to further catalytic upgrading, or liquid transportation fuel (or a blend component thereof).

Referring again to the embodiment outlined in FIG. 3, the first fraction 313 enters an inlet of the first activation reactor 325. The temperature within the first activation reactor (termed the second temperature, typically measured at the inlet of the first activation reactor) is maintained in the range from 500° C. to 650° C.; optionally, the temperature is maintained in the range from 525° C. to 625° C.; optionally, the temperature is maintained in the range from 525° C. to 600° C.; optionally, the temperature is maintained in the range from 550° C. to 600° C.; optionally, the temperature is maintained in the range from 550° C. to 575° C.

The second fraction 317 enters an inlet of the second activation reactor 335. The temperature within the second activation reactor (termed the second temperature, typically measured within the inlet of the second activation reactor) is maintained in the range from 500° C. to 650° C. Optionally, the temperature is maintained in the range from 525° C. to 650° C. Optionally, the temperature is maintained in the range from 550° C. to 625° C. Optionally, the temperature is maintained in the range between 575° C. and 600° C. Lower pressure favors the conversion of light alkanes to light olefins. Thus, the first activation reactor 325 and second activation reactor 335 are generally maintained at a pressure ranging from 15 psia to 165 psia. In certain embodiments, the pressure is maintained in the range from 15 psia to 50 psia.

In certain embodiments, the first temperature is lower than the second temperature. Optionally, the first temperature may be at least 10° F. lower, at least 20° F. lower, at least 25° F. lower, at least 30° F. lower, at least 35° F. lower, at least 40° F. lower, at least 45° F. lower or at least 50° F. lower than the second temperature.

A first effluent 336 leaves the first activation reactor 320, while a second effluent 337 leaves the second activation reactor 330. Each effluent is conveyed to condenser 340, which may comprise one or more functions including a condenser, splitter, compressor and pump. Condenser 340 is operable to receive and combine the first effluent 336 and the second effluent 337 and condense liquids from the mixture to produce a mixed liquid hydrocarbons and a mixed effluent 345 (that is gaseous). The mixed liquid hydrocarbons 342 are removed while the mixed effluent 345 is then compressed either within the condenser 340 or by a separate compressor located immediately downstream (not depicted), and then conveyed to an aromatic alkylation reactor 350 containing aromatic alkylation catalyst 355.

Speaking generally, the alkylation reactor is maintained at a feed inlet temperature and pressure suitable to facilitate the catalytic alkylation of aromatics present in the mixed effluent. The aromatics that are alkylated may be produced by aromatization that takes place in the first or second activation reactor, may be present in the feed stream for the process, or a combination of these possibilities. These aromatics are alkylated by olefins that are largely produced by the activation of alkanes in the first and second activation reactors. Alkylation of aromatics in the alkylation reactor produces larger hydrocarbons comprising at least seven carbons that are preferably characterized by a boiling point that is in the boiling point range of a liquid transportation fuel (e.g., gasoline or diesel). Typically, the alkylation effluent comprises an increased percentage of alkylated aromatic compounds comprising from seven to nine carbon atoms. Optionally, the larger hydrocarbons also are characterized by a lower Reid vapor pressure and an increased octane rating.

The alkylation reactor is generally maintained at a pressure in a range from 14 psia to 800 psia, optionally in the range from 50 psia to 600 psia. The alkylation reactor is typically maintained at a temperature (measured within the alkylation reactor inlet) in a range from 150° C. to 350° C., optionally between 200° C. to 350° C. Typically, flow thorough the alkylation reactor is maintained at a weighted hourly space velocity (WHSV) in the range from 0.5 $hr^{-1}$ to 10 $hr^{-1}$ on an olefins basis. Optionally, the WHSV is in the range from 0.5 $hr^{-1}$ to 2.0 $hr^{-1}$. While higher overall throughput is desirable, ideally the chosen WHSV allows for conversion of at least 85% of hydrocarbons present in the mixed effluent at the selected operating temperature and pressure. The catalytic conversion occurring in the alkylation reactor produces an aromatic alkylation reactor effluent that typically comprises at least 30 wt. % (preferably, at least 40 wt %) of hydrocarbon molecules that are characterized by a boiling-point in the range of a liquid transportation fuel.

Speaking generally, the alkylation catalyst may comprise any catalyst characterized as either Brønsted or Lewis acidic. A wide variety of catalysts have been found to promote aromatic alkylation including, but not limited to, aluminum chloride, phosphoric acid, sulfuric acid, hydrofluoric acid, silica, alumina, sulfated zirconia, zeolites (including, for example, ZSM-5, ZSM-3, ZSM-4, ZSM-18, ZSM-20, zeolite-beta, H-Y, MCM-22, MCM-36 and MCM-49). In certain embodiments, the alkylation catalyst simultaneously promotes alkylation of aromatics and oligomerization of olefins present in the mixed effluent.

Referring again to the embodiment depicted in FIG. 3, the alkylation reactor effluent 357 is conveyed to a second separator 360 that separates the alkylation effluent 357 into two fractions: a light hydrocarbons fraction 365 comprising C1-C4 hydrocarbons and $H_2$, and a condensed liquid hydrocarbons 368 comprising hydrocarbons containing at least five carbon atoms (C5+) that may be utilized directly as a blend component of a liquid transportation fuel or additionally processed prior to blending into a liquid transportation fuel. Preferably, the alkylation effluent comprises an increased quantity (or increased wt %) of alkylated aromatics containing from seven to nine carbon atoms. Preferably, these alkylated aromatics are monocyclic aromatic hydrocarbons.

In the embodiment depicted in FIG. 3, the condensed liquid hydrocarbons 368 is conveyed to a third separator 370 that is optionally a naphtha stabilizer. The third separator 370 is operable to remove a recycle fraction 372 (comprising predominantly alkanes and olefins containing four to six carbon atoms) from the condensed liquid hydrocarbons 368 in order to decrease Reid vapor pressure and increase octane rating. The resulting liquid hydrocarbon product 374 predominantly comprises hydrocarbon molecules that are characterized by a boiling-point in the range of a liquid transportation fuel, such as, but not limited to, gasoline, diesel and jet fuel. The recycle fraction 372 is mixed with feed stream 302 at a point that is upstream from the first separation unit 310. This recycling also serves to indirectly recycle any benzene present in the recycled fraction 372 to the alkylation reactor 350, as the benzene would be relatively unreactive in the second activation reactor 330. Optionally, a portion of the second fraction that is stored in storage vessel 327 may be directed via excess second fraction conduit 319 to be combined with the liquid hydrocarbon product 374.

Speaking more generally, in certain embodiments the liquid hydrocarbon product may be hydrotreated in a hydrotreating reactor containing a hydrotreating catalyst in order to reduce olefins and aromatic content in the liquid hydrocarbon product, as well as to remove nitrogen-containing and sulfur-containing compounds. The hydrotreating reactor contains at least one hydrotreating catalyst (such as, for example, NiMo, CoMo, etc.) or a precious metal catalyst (such as $Pt/Al_2O_3$, $Pd/Al_2O_3$, or Pd/C, etc) and is maintained at a pressure and temperature suitable for facilitating hydrotreating catalytic reactions. Such processes are conventional in nature and therefore will not be described in greater detail here.

Again, referring to the embodiment depicted in FIG. 3, light hydrocarbons fraction 365 predominantly comprises hydrogen as well as C1-C4 hydrocarbons that were not converted in the alkylation reactor 355. Light hydrocarbons gas 365 leaves the second separator 360 and is optionally conveyed to a fourth separator 366 that utilizes a conventional separation technology (such as, but not limited to, pressure swing adsorption technology, membrane separation technology, etc.) to separate hydrogen from light hydrocarbons to produce a hydrogen stream 367 and a C1-C4 light paraffins stream 369 that is optionally combusted to provide at least a portion of the heat required for the process (not depicted), or recycled to serve as a diluent that is mixed with at least one of: the first fraction 313 and the second fraction 318.

Certain embodiments comprise mixing a diluent with the first fraction and/or the second fraction prior to contacting with an activation catalyst. The diluent may be added in a ratio ranging from 10:1 to 1:10 molar ratio relative to the quantity of pentanes feed stream fed to each activation reactor. The diluent may be added at any point that is upstream from, or within, the first or second activation reactors.

The diluent may comprise any substance that is less chemically-reactive than the constituents present in the first fraction or the second fraction at the conditions of temperature and pressure that are maintained within the first and second activation reactors. This is intended to prevent the diluent from reacting with the first and second activation catalysts. Such properties are found in a large number of substances that are fully within the grasp of one having experience in the art. In certain embodiments, the diluent may comprise a C1-C4 light paraffins, including recycling C1-C4 light paraffins produced by the processes and systems described herein. In certain embodiments, the diluent may comprise any of methane, ethane, propane, butanes, benzene, toluene, xylenes, alkyl- or dialkyl-benzenes, naphthenes, C2-C5 olefins, and combinations thereof.

The presence of diluent during catalytic activation (i.e., activation) provides numerous advantages. First, it effectively decreases the concentration of the first fraction within the first activation reactor, decreases the concentration of the second fraction within the second activation reactor, or both. This results in a small increase in the total conversion of pentanes (typically approximately 5-6 wt. %) to olefins or aromatics within each activation reactor. However, it increases the selectivity toward the production of olefins in both the first and second effluent, while slightly decreasing the selectivity toward aromatics. Adjusting the ratio of diluent to feed stream changes the ratio of olefins to aromatics exiting the reactor, thereby providing a valuable point of operational control for downstream processes. Typically, the optimal molar production ratio of olefins to aromatics ranges from about 0.5:1 to about 1.5:1, in order to maximize the value captured in the olefins intermediates during the alkylation in the alkylation reactor. Mono-alkylated aromatics exhibit beneficial (increased) octane rating and vapor pressure for application as blending components in certain transportation fuels such as gasoline. In contrast, di-alkyl and tri-alkyl aromatics comprising more than nine carbon atoms are not well-suited for blending into gasoline, and exhibit nonoptimal cetane number for blending into diesel.

Addition of a diluent also advantageously favors the production of value-added olefins relative to C1-C4 light paraffins, and also mitigates dimerization of C5 hydrocarbons to form durene (1,2,4,5-tetramethylbenzene), a byproduct notorious for precipitating as a solid out of gasoline blends.

EXAMPLES

The following examples are representative of one embodiment of the inventive processes and systems disclosed herein, and the scope of the invention is not intended to be limited to the embodiment specifically disclosed. Rather, the scope is intended to be as broad as is supported by the complete disclosure and the appending claims.

Example 1

The graphs below illustrate differences in activation reactivity for n-C5 and i-C5. Feed streams were utilized that comprised either 100 wt. % i-C5 (i-C5) or 100 wt. % of n-C5 (n-C5). Feed streams comprising essentially 100% of a single pentane isomer are representative of separated pentanes streams due to preliminary data showing that a mixed pentanes stream can be separated into i-C5 and n-C5 fractions of approximately 93% purity when separating is performed according to the methods disclosed herein. The catalyst was ⅛" extrudate consisting of 50 wt. % alumina binder and 50 wt. % ZSM-5 zeolite, and experiments were conducted at a WHSV of 1.3 hr$^{-1}$ at 1 atm. Results were averaged over the total time on stream of 16 hr.

Figure 4:
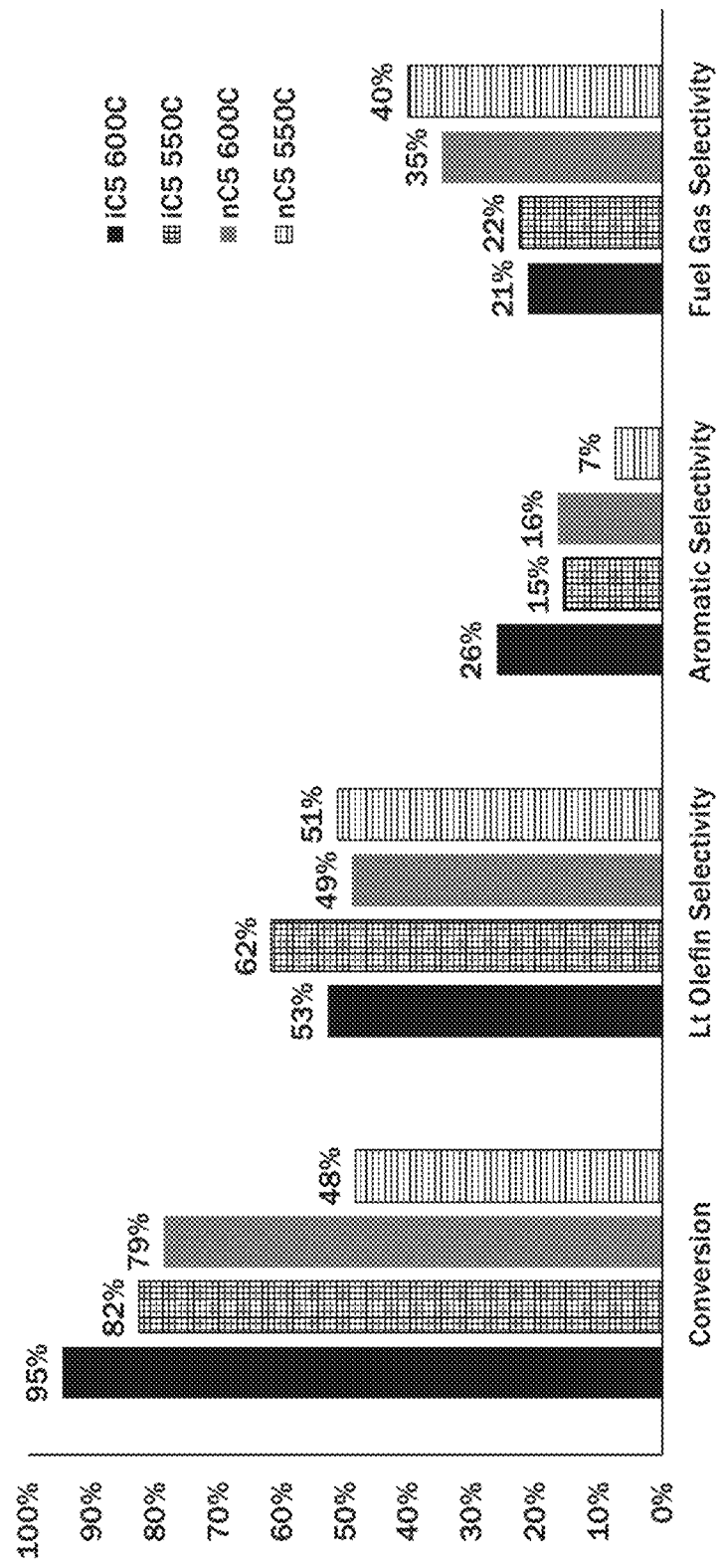
FIG. 4 is a bar graph depicting product selectivity resulting from catalytic activation of either n-pentane or iso-pentane at two different temperatures.

FIG. 4 is a bar graph depicting the results of catalytically activating each fraction at either 550° C. or 600° C. The graph depicts, as percentages, the total catalytic conversion of each feed stream (first column), the selectivity to light olefins as product (second column), the selectivity to aromatics as product (third column) and the selectivity to C1-C4 light paraffins (defined as non-olefins hydrocarbons containing from one to four carbon atoms), fourth column. Selectivity was calculated on a % carbon basis, relative to the portion of the feed stream fraction that was converted.

The results demonstrate that total conversion of a 100% n-C5 fraction at 600° C. was 79% and a similar 82% conversion was observed when activating a 100% i-C5 feed stream at 50° C. cooler (i.e., 550° C.). Activating the first fraction at 550° C. (instead of 600° C.) also increased the selectivity towards the production of olefins while decreasing the selectivity of conversion toward aromatics. Lastly, these changes in selectivity caused no significant increase in the production of byproduct C1-C4 light paraffins. However, activation of n-C5 at 550° C. was generally unsuitable, and resulted in a 31% decrease in total conversion, and a noticeable increase in the production of C1-C4 light paraffins.

Example 2

A 100% i-C5 feed stream was upgraded by first contacting it with a zeolite activation catalyst, followed by contacting a zeolite oligomerization catalyst. Activation was conducted by contacting the feed stream with ⅛ in. diameter catalyst extrudate consisting of 50 wt. % alumina binder and 50 wt. % ZSM-5 zeolite catalyst at a temperature of 579° C., and a WHSV of 2.6 hr$^{-1}$ at 1 atm. Oligomerization was conducted by contacting the activation effluent with a ZSM-5 catalyst in a reactor where the inlet temperature for the feed stream was maintained at 250° C., the pressure was 1 atm, and the WHSV for the feed stream was 1.3 hr$^{-1}$. Results were time-averaged over 16 hours. The table shows the product distribution following conversion along with the selectivity to olefins and liquid product. The term "selectivity" indicates the percentage of the catalytically converted feed stream that was converted to a particular product.

TABLE 2

Upgrading pentanes by activation alone or activation plus oligomerization.

|  | Activation | Activation + Oligomerization |
|---|---|---|
| Total Conversion (wt. %) | 88 | 87 |
| C1-C4 Light paraffins Yield | 32 | 32 |
| Upgraded Product Yield (wt. %) | 55 | 54 |
| Total Coke Yield (wt. %) | 0.1 | 0.1 |
| Light Olefin Yield (wt. %) | 42 | 16 |
| Light Olefin Selectivity (wt. %) | 48 | 19 |
| Liq. Yield (wt. %) | 13 | 38 |
| Liq. Product Selectivity (wt. %) | 15 | 44 |

The data in Table 2 show that the subjecting the effluent from the first activation reactor to a subsequent oligomerization step in a second activation reactor increased the liquid product yield from 13 wt. % to 38 wt. %. This liquid product yield represents a liquid product suitable for blending into a liquid transportation fuel such as gasoline (up from 13 wt. % prior to oligomerization), and that selectivity to liquid product for the portion of the feed stream that was converted was 44 wt. %. Undesirable C1-C4 light paraffins production was limited to 32 wt. % of the original feed stream, which in a commercial embodiment would preferably be recycled to process to be either activated or to serve as a diluent in at least one of the activation reactors. Further, the final product only comprised 16 wt. % of light olefins, (primarily ethylene), which may be recycled to the process, or diverted to be utilized in any of a variety of conventional processes.

Example 3

A 100 wt. % i-C5 feed stream was upgraded by first contacting it with a zeolite activation catalyst, followed by contacting the effluent with a zeolite alkylation catalyst. Activation was conducted by contacting the feed stream with a ⅛ in. diameter catalyst extrudate consisting of 50 wt. % alumina binder and 50 wt. % ZSM-5 zeolite catalyst in an activation reactor. The temperature of the activation reactor at the inlet for the feed stream was 579° C., the pressure was 1 atm, and the WHSV for the feed stream was 2.6 $hr^{-1}$. Alkylation was then conducted by contacting the effluent with a ZSM-5 catalyst in a reactor where the temperature at the inlet for the feed stream was 230 C and the WHSV of the feed stream was 1.3 $hr^{-1}$ at 1 atm. Results were time-averaged over 16 hours. The table shows the product distribution following conversion along with the selectivity to olefins and liquid product. The term "selectivity" indicates the percentage of the catalytically converted feed stream that was converted to a particular product.

TABLE 3

Upgrading pentanes by activation only or activation followed by alkylation.

|  | Activation | Activation + Alkylation |
|---|---|---|
| Total Conversion (wt. %) | 87 | 87 |
| Light paraffins Yield (wt. %) | 32 | 32 |
| Upgraded Product Yield (wt. %) | 55 | 55 |
| Total Coke Yield (wt. %) | 0.1 | 0.2 |
| Light Olefin Yield (wt. %) | 42 | 12 |
| Light Olefin Selectivity (wt. %) | 48 | 14 |
| Liquid Yield (wt. %) | 13 | 42 |
| Liquid Product Selectivity (wt. %) | 15 | 48 |

The data in Table 3 show that subjecting the effluent to a subsequent alkylation step increased the liquid product yield from 13 wt. % to 42 wt. %. This liquid product is suitable for blending into a liquid transportation fuel such as gasoline, and possesses an increased research octane number, a suitable distillation T50 and endpoint, and low vapor pressure. Selectivity to liquid product for the portion of the feed stream that was converted increased from 15 wt. % to 48 wt. %. Undesirable C1-C4 light paraffins production was limited to 32 wt. % of the original feed stream. Further, the final product only comprised 14 wt. % of light olefins. These olefins may be recycled to the process or diverted to be utilized in any of a variety of conventional processes.

Note that the results shown in the above table may underestimate the total percentage of a mixed pentanes feed stream that would be available for blending into a liquid transportation fuel, as a mixed pentanes feed stream (or other light hydrocarbon feed stream, such as natural gasoline) may also include an excess quantity of C5/C6+ that would not be either catalytically cracked or introduced into the alkylation reactor. This excess quantity of C5/C6+ is suitable for direct blending into the liquid hydrocarbon product. In certain embodiments, a portion of the nC5/C6+ fraction is diverted when necessary to achieve the desired 0.5:1 to 1.5:1 olefins to aromatic ratio that maximizes production of mono-alkylated aromatics in the alkylation reactor.

Example 4

The following table shows the viability of a product produced by one embodiment of the inventive processes and systems described herein. The composition of a conventional commercial reformate product (Comparative Example) following processing to remove light components (including benzene), is compared with the composition of an unprocessed product produced by an embodiment that included activation in a first reactor followed by alkylation in a second reactor. The temperature of the first reactor at the inlet for the feed stream was maintained at 600° C. and a WHSV=2.6 $hr^{-1}$, while the temperature of the alkylation reactor (at the inlet for the feed stream) was maintained at 230° C. and a WHSV=1.3 $hr^{-1}$. Results shown represent average wt. % for each product over 16 hours, and all reactions were performed at 1 atm. RON=road octane number; MON=motor octane number.

TABLE 4

Product distributions of identical iC5 isomer streams subjected to catalytic activation alone (Column 1) or catalytic activation followed by catalytic alkylation (Column 2).

| Component/Property | Comparative Example (A Commercial Reformate Composition) | Inventive Example (Activation + Alkylation) |
|---|---|---|
| n-Paraffins (wt. %) | 4.7 | 2.9 |
| Iso-paraffins (wt. %) | 15.9 | 9.5 |
| Aromatics (wt. %) | 77.9 | 67.6 |
| Mono-alkyl aromatics (wt. %) | 75.0 | 64.4 |
| n-Olefins (wt. %) | 0.1 | 1.2 |
| Iso-Olefins (wt. %) | 0.2 | 4.4 |
| Estimated RON | 96.84 | 98.3 |
| Estimated MON | 91.46 | 89.9 |
| Avg. Molecular Weight | 107.62 | 103.50 |
| Avg. Specific Gravity | 0.82 | 0.80 |
| Avg. API Gravity @15.5° C. | 40.6° | 41.5° |
| Reid Vapor Pressure (kPa) | 19.2 | 44.8 |
| Total Hydrogen | 11.01 | 10.80 |
| Carbon:Hydrogen Ratio | 8.08 | 7.90 |

Example 5

A feed stream comprising 100 wt. % of i-C5 was fed at a WHSV of 1.3 $hr^{-1}$ to a reactor containing ⅛" extrudate consisting of 50 wt. % alumina binder and 50 wt. % ZSM-5 zeolite activation catalyst to produce an effluent comprising light olefins, aromatics and light paraffins. The temperature of the reactor (at the inlet for the feed stream) was maintained at 600° C. and 20 psig (2.4 Bar) and results were time-averaged for 16.5 hr. For certain reactions, methane diluent was co-fed along with i-C5 at a methane:i-C5 molar ratio of 2:1 and 4:1.

Figure 5:
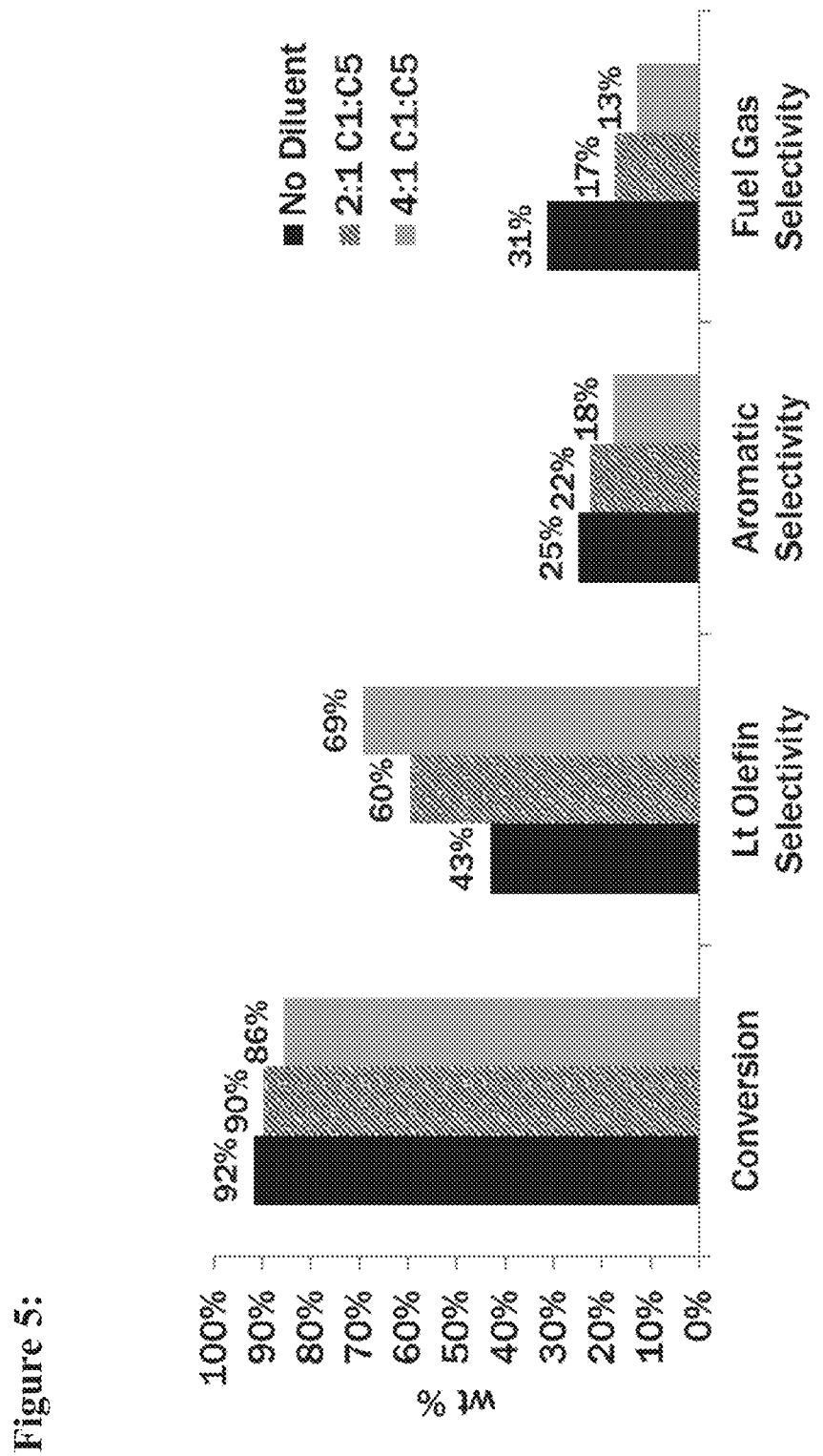
FIG. 5 is a bar graph showing the effect of methane diluent on the total conversion of the feed stream, as well as the selectivity of the conversion toward light olefins, aromatics, and byproduct C1-C4 light paraffins.

FIG. 5 is a bar graph that shows the effect of the diluent on the total conversion of the feed stream, as well as the selectivity of the conversion toward light olefins, aromatics, and byproduct C1-C4 light paraffins. Increasing the ratio of diluent did not significantly decrease conversion but correlated with a large increase in selectivity to light olefins production and greatly diminished selectivity to production of C1-C4 light paraffins. Meanwhile, only a small drop in selectivity to aromatics production were observed. All of these results are advantageous to the process, particularly in certain embodiments where the mixed effluent is immediately utilized as feed stream for either an oligomerization or alkylation process. In certain embodiments that comprise an oligomerization process, diluent is added to the feed stream at a ratio that maximizes light olefins production, providing an advantageous feed stream for the oligomerization catalyst. In certain embodiments that comprise an aromatic alkylation process, diluent can be added to the feed stream at a ratio that produces a first effluent comprising olefins and aromatics at a ratio (typically between 0.5:1 and 1.5:1 by mole) that provides an advantageous feed stream for an aromatic alkylation process.

Example 6

A feed stream comprising 100 wt. % of i-C5 was fed at a WHSV of 1.3 hr$^{-1}$ to an activation reactor containing ⅛" extrudate consisting of 50 wt. % alumina binder and 50 wt. % ZSM-5 zeolite activation catalyst to produce an effluent comprising light olefins, aromatics and C1-C4 light paraffins. The temperature of the reactor (at the inlet for the feed stream) was maintained at 550° C. and 20 psig (2.4 Bar) and results were time-averaged for 16 hr. For certain reactions, a diluent comprising methane was co-fed along with i-C5 at a methane:i-C5 molar ratio of 4:1 and 8:1.

Figure 6:
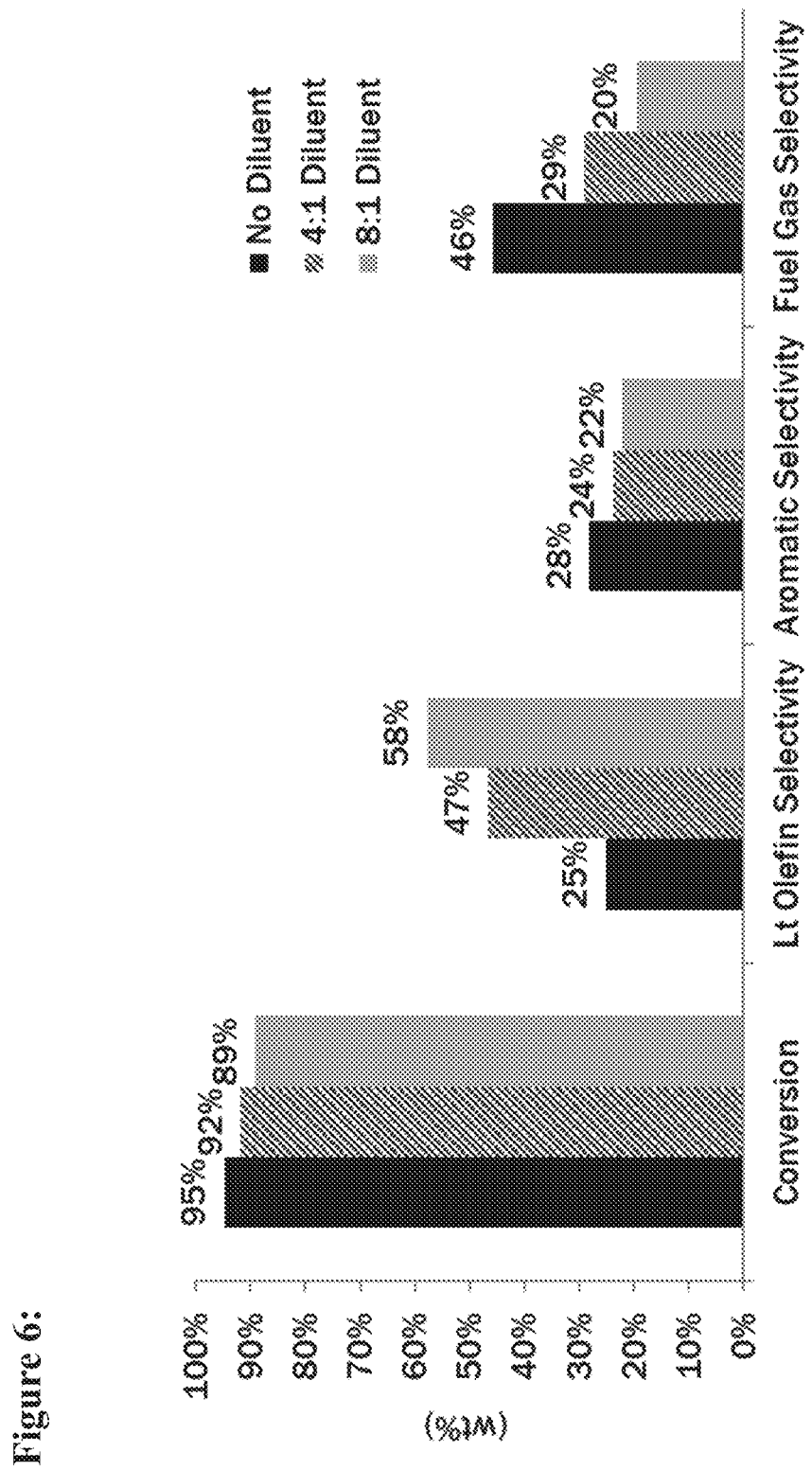
FIG. 6 is a bar graph showing the effect of methane diluent on the total conversion of the feed stream, as well as the selectivity of the conversion toward light olefins, aromatics, and byproduct C1-C4 light paraffins.

FIG. 6 is a bar graph that shows the effect of the diluent on the total conversion of the feed stream, as well as the selectivity of the conversion toward light olefins, aromatics, and byproduct C1-C4 light paraffins. As in EXAMPLE 5, increasing the ratio of inert diluent did not significantly decrease conversion, but correlated with a large increase in selectivity to light olefins production and greatly diminished selectivity to production of C1-C4 light paraffins. Meanwhile, only a small drop in selectivity to aromatics production were observed. All of these results are advantageous to the process, particularly in certain embodiments where the mixed effluent is immediately utilized as feed stream for either an oligomerization or alkylation process.

In closing, it should be noted that the discussion of any reference is not an admission that it is prior art to the present disclosure, in particular, any reference that may have a publication date after the priority date of this application. Although the systems and processes described herein have been described in detail, it is understood that various changes, substitutions, and alterations can be made without departing from the spirit and scope of the invention as defined by the following claims.

Definitions

In the present disclosure, the term "conversion" is defined as any of the chemical reactions that occur during upgrading of hydrocarbons to liquid transportation fuels. Examples of such reactions include, but are not limited to: oligomerization, aromatization, dehydrogenation, alkylation, hydrogenation and cracking.

We claim:

1. A method for converting a feedstock comprising pentanes to produce a liquid transportation fuel or a blend component thereof, comprising:
a) providing a hydrocarbon feed stream comprising at least 50 wt. % pentanes, including both n-pentane and isopentane, wherein the hydrocarbon feed stream further comprises less than 10 wt. % of hydrocarbons containing four or fewer carbons;
b) at least partially separating various constituents in the hydrocarbon feed stream according to each constituent's vapor pressure, to produce:
i. a first fraction comprising at least 80% of the isopentane present in the feed stream, and at least 90% of hydrocarbons present in the feed stream that are characterized by a vapor pressure equal to or greater than the vapor pressure of isopentane;
ii. a second fraction that comprises at least 80% of the n-pentane present in the feed stream and at least 90% of any hydrocarbons containing six or more carbons that were in the feed stream;
c) contacting the first fraction with a first activation catalyst at conditions comprising a first temperature and first pressure that facilitate conversion of at least a portion of the first fraction by the first activation catalyst to a first effluent comprising olefins containing from two to five carbon atoms, monocyclic aromatics and unconverted alkanes;
d) contacting at least a portion of the second fraction with a second activation catalyst at a second temperature and second pressure that facilitate conversion of at least a portion of the second fraction by the second catalyst to produce a second effluent comprising olefins containing from two to five carbon atoms, monocyclic aromatics and unconverted alkanes,
wherein the first temperature is lower than the second temperature;
e) combining at least a portion of the of the first effluent and the second effluent to produce a mixed effluent that is at least partially condensed to produce a mixed liquid hydrocarbons fraction and a light hydrocarbons fraction, wherein the mixed liquid hydrocarbons comprises at least 80 wt % of one or more of pentene, monocyclic aromatics and unreacted alkanes containing at least five carbon atoms, wherein the light hydrocarbons comprises at least 80 wt. % hydrocarbons containing four or fewer carbon atoms and hydrogen, and wherein the mixed liquid hydrocarbons comprises the liquid transportation fuel or a blend component thereof.

2. The method of claim 1, further comprising separating the mixed liquid hydrocarbons into an aromatics fraction and C5/C6 hydrocarbons fraction, wherein the aromatics fraction comprises monocyclic aromatics and the unreacted C5/C6 hydrocarbons fraction comprises alkanes and olefins containing from five to six carbons.

3. The method of claim 2, wherein a portion of the second fraction is not contacted with the second catalyst and is blended with the aromatics fraction.

4. The method of claim 1, wherein the hydrocarbon feed stream comprises less than 5 wt. % of hydrocarbons containing four or fewer carbon atoms.

5. The method of claim 1, wherein the hydrocarbon feed stream comprises at least 60 wt. % pentanes.

6. The method of claim 1, wherein the first temperature is at least 25° C. lower than second temperature.

7. The method of claim 1, wherein the first temperature is at least 50° C. lower than second temperature.

8. The method of claim 1, wherein the weight hourly space velocity of the first fraction as it contacts the first catalyst is higher than the weight hourly space velocity of the second fraction as it contacts the second catalyst.

9. The method of claim 1, wherein the first catalyst differs from the second catalyst in at least one of chemical composition and structural composition.

10. The method of claim 1, further comprising adding a diluent to at least one of: the first fraction prior to the contacting of c) and the second fraction prior to the contacting of d), wherein the diluent is characterized as less likely to react with the first catalyst than molecules present in the first fraction at the conditions of temperature and pressure that are maintained in the first reactor and/or wherein the diluent is characterized as less likely to react with the second catalyst than molecules present in the second fraction at the conditions of temperature and pressure that are maintained in the second reactor.

11. The method of claim 10, wherein adding the diluent alters the specificity of at least one of the first activation catalyst and the second activation catalyst to increase the production of olefins, decrease the production of aromatics, or combinations thereof, thereby increasing the ratio of olefins to aromatics in the mixed effluent.

12. The method of claim 10, wherein the diluent is added in an amount that is effective to provide an olefins to aromatics ratio in the range of 0.5 to 2.0 in the mixed effluent.

13. The method of claim 10, wherein the diluent is added in an amount that is effective to provide an olefins to aromatics ratio in the range of 0.5 to 1.0 in the mixed effluent.

14. The method of claim 10, wherein the diluent is selected from methane, ethane, propane, butanes, benzene, toluene, xylenes, alkyl- or dialkyl-benzenes, naphthenes, C2-C5 olefins, and combinations thereof.

15. The method of claim 1, further comprising adding a diluent to at least one of: the first fraction prior to the contacting of c) and the second fraction prior to the contacting of d), wherein the diluent does not react catalytically with the first activation catalyst at the conditions of temperature and pressure that are maintained in the first reactor and/or wherein the diluent does not react catalytically with the second activation catalyst at the conditions of temperature and pressure that are maintained in the second reactor.

* * * * *